United States Patent [19]

Lamm et al.

[11] Patent Number: 5,536,840
[45] Date of Patent: Jul. 16, 1996

[54] PROCESS OF PREPARING DIAMINOPYRIDINE COMPOUNDS

[75] Inventors: Gunther Lamm, Hassloch; Hermann Loeffler, Speyer; Helmut Reichelt, Neustadt, all of Germany

[73] Assignee: BASF Aktiengesellschaft, Ludwigshafen, Germany

[21] Appl. No.: 244,721

[22] PCT Filed: Mar. 10, 1993

[86] PCT No.: PCT/EP93/00538

§ 371 Date: Jun. 17, 1994

§ 102(e) Date: Jun. 17, 1994

[87] PCT Pub. No.: WO94/20469

PCT Pub. Date: Sep. 15, 1994

[51] Int. Cl.⁶ .............. C07D 213/84; C07D 213/85; C07D 405/12
[52] U.S. Cl. .............. 546/289; 546/282.1; 546/283.4
[58] Field of Search .............. 546/268, 283, 546/289

[56] References Cited

U.S. PATENT DOCUMENTS

| | | | |
|---|---|---|---|
| 3,853,895 | 12/1974 | Lamm et al. | 260/294.9 |
| 3,980,659 | 9/1976 | Fleckenstein et al. | 260/294.8 |
| 4,325,870 | 4/1982 | Bühler et al. | 260/156 |

FOREIGN PATENT DOCUMENTS

| | | | |
|---|---|---|---|
| 2260827 | 7/1974 | Germany | 546/289 |
| 2916319 | 11/1980 | Germany | 546/289 |

Primary Examiner—Zinna Northington Davis
Attorney, Agent, or Firm—Oblon, Spivak, McClelland, Maier & Neustadt

[57] ABSTRACT

A process for preparing diaminopyridines of the formula

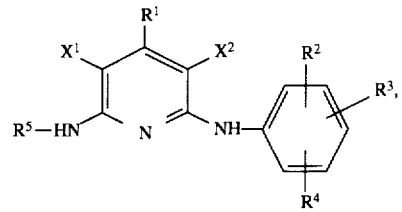

where one of the two radicals $X^1$ and $X^2$ is hydrogen, $C_1$–$C_4$-alkyl, halogen or nitro and the other is cyano, $R^1$ is hydrogen, $C_1$–$C_4$-alkyl or phenyl, $R^2$ and $R^3$ are each hydrogen, $C_1$–$C_4$-alkyl or $C_1$–$C_4$-alkoxy, $R^4$ is hydrogen or $C_1$–$C_4$-alkyl, and $R^5$ is optionally substituted $C_1$–$C_{10}$-alkyl, $C_3$–$C_4$-alkenyl or $C_5$–$C_7$-cycloalkyl, by reacting dichloropyridines of the formula

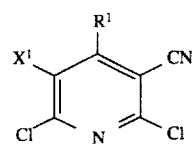

(II)

in a first step with an amine of the formula $R^5$-$NH_2$ at from 10° to 80° C. in the presence of a base and of an inert organic diluent and/or water, then removing the diluent and thereafter, with or without prior intermediate isolation of the reaction product, comprises carrying out the second step in a melt at from 90° to 165° C. and at a pH from 3.5 to 6.5 using from 1.3 to 3 mol of aniline IV are used per mole of dichloropyridine II.

4 Claims, No Drawings

PROCESS OF PREPARING DIAMINOPYRIDINE COMPOUNDS

This application is a 371 of PCT/EP93/00538, filed Mar. 10, 1993.

The present invention relates to a novel process for preparing 2,6-diaminocyanopyridines by reacting the 2,6-dichloro compounds with amines.

U.S. Pat. No. 3,853,895 discloses the preparation of 2,6-diaminopyridines. However, the manner of preparation described therein is unsatisfactory, since large amounts of amine are required and, what is more, the target products are obtained only in a low yield.

Furthermore, DE-A-2 260 827, DE-A-2 916 319 and U.S. application Ser. No. 3,980,659 describe the preparation of 2,6-diaminocyanopyridines using the corresponding dichloro or aminomonochloro compounds as starting materials.

It is an object of the present invention to provide a novel process for preparing 2,6-diaminocyanopyridines which likewise starts from the 2,6-dichloro compounds and gives the target products in a simple manner and in high yield and purity.

We have found that this object is achieved in an advantageous manner by a process for preparing diaminopyridines of the formula I

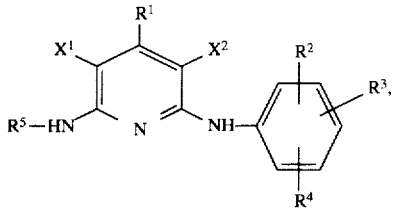

where
one of the two radicals $X^1$ and $X^2$ is hydrogen, $C_1$–$C_4$-alkyl, halogen or nitro and the other is cyano,
$R^1$ is hydrogen, $C_1$–$C_4$-alkyl or phenyl,
$R^2$ and $R^3$ are each independently of one another hydrogen, $C_1$–$C_4$-alkyl or $C_1$–$C_4$-alkoxy,
$R^4$ is hydrogen or $C_1$–$C_4$-alkyl, and
$R^5$ is $C_1$–$C_{10}$-alkyl which may be interrupted by from 1 to 3 oxygen atoms in ether function and is optionally hydroxyl-, $C_1$–$C_4$-alkanoyloxy-, phenoxy-, phenyl-, tetrahydrofuranyl- or tetrahydropyranyl-substituted, $C_3$–$C_4$-alkenyl or $C_5$–$C_7$-cycloalkyl,
by reacting dichloropyridines of the formula II

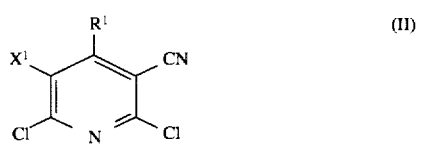

where $R^1$ and $X^1$ are each as defined above, with amines by reacting in a first step a dichloropyridine of the formula II with an amine of the formula III

$R^5$—NH$_2$ (III)

where $R^5$ is as defined above, at from 10° to 80° C. in the presence of a base and of an inert organic diluent and/or water, then removing the diluent and thereafter, with or without prior intermediate isolation of the reaction product, reacting it in a second step with an aniline of the formula IV

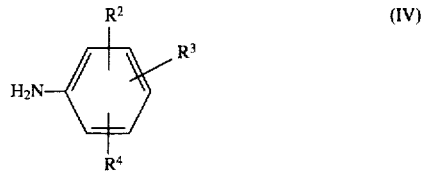

where $R^2$, $R^3$ and $R^4$ are each as defined above, which comprises carrying out the second step in a melt at from 90° to 165° C. and at a pH from 3.5 to 6.5 using 1.3 to 3 mol of aniline IV per mole of dichloropyridine II.

Any alkyl appearing in the abovementioned formulae may be not only straight-chain but also branched.

$R^1$, $R^2$, $R^3$, $R^4$, $R^5$, $X^1$ and $X^2$ are each for example methyl, ethyl, propyl, isopropyl, butyl, isobutyl or sec-butyl.

$R^4$ may also be for example methoxy, ethoxy, propoxy, isopropoxy, butoxy, isobutoxy or sec-butoxy.

$R^5$ may also be for example pentyl, isopentyl, neopentyl, tert-pentyl, hexyl, 2-methylpentyl, heptyl, octyl, 2-ethylhexyl, isooctyl, nonyl, isononyl, decyl, benzyl, 1- or 2-phenylethyl, 2- or 3-phenylpropyl, 3-phenylprop-2-yl, 2-hydroxyethyl, 2-hydroxypropyl, 3-hydroxypropyl, 3-hydroxyprop-2-yl, 2-hydroxybutyl, 4-hydroxybutyl, 5-hydroxypentyl, 6-hydroxyhexyl, 2-methoxyethyl, 2-ethoxyethyl, 2-propoxyethyl, 2-isopropoxyethyl, 2-butoxyethyl, 2- or 3-methoxypropyl, 2- or 3-ethoxypropyl, 2- or 3-propoxypropyl, 2- or 3-butoxypropyl, 2- or 4-methoxybutyl, 2- or 4-ethoxybutyl, 2- or 4-propoxybutyl, 2- or 4-butoxybutyl, 3,6-dioxaheptyl, 3,6-dioxaoctyl, 4,8-dioxanonly, 3,7-dioxaoctyl, 3,7-dioxanonyl, 4,7-dioxaoctyl, 4,7-dioxanonyl, 4,8-dioxadecyl, 3,6,9-trioxadecyl, 3,6,9-trioxaundecyl, 4,8,12-trioxatridecyl, 2-phenoxyethyl, 2-phenoxypropyl, 3-phenoxypropyl, 2-phenoxybutyl, 4-phenoxybutyl, 5-phenoxypentyl, 6-phenoxyhexyl, 5-hydroxy-3-oxapentyl, 8-hydroxy-4-oxaoctyl, 6-phenoxy-4-oxahexyl, 2-formyloxyethyl, 2-acetyloxyethyl, 2-propionyloxyethyl, 2- or 3-formyloxypropyl, 2- or 3-acetyloxypropyl, 2- or 3-propionyloxypropyl, 2- or 4-formyloxybutyl, 2- or 4-acetyloxybutyl, 2- or 4-propionyloxybutyl, 2-(tetrahydropyran-4-yl)ethyl, 2- or 3-(tetrahydropyran-4-yl)-propyl, 2- or 4-(tetrahydropyran-4-yl)butyl, prop-2-en-1-yl, but-2-en-1-yl, 2-methylprop-2-en-1-yl, cyclo-pentyl, cyclohexyl or cycloheptyl.

$X^1$ and $X^2$ may each also be example fluorine, chlorine and bromine.

Preference is given to a process for preparing diaminopyridines of the formula I where $X^1$ is hydrogen and $X^2$ is cyano.

Further preference is given to a process for preparing diaminopyridines of the formula I where $R^1$ is methyl.

Further preference is given to a process for preparing diaminopyridines of the formula I where $R^2$, $R^3$ and $R^4$ are each hydrogen.

Further preference is given to a process for preparing diaminopyridines of the formula I where $R^2$ is methyl or methoxy and $R^3$ and $R^4$ are each hydrogen or methyl or where $R^2$ and $R^3$ are each methyl and $R^4$ is hydrogen.

Further preference is given to a process for preparing diaminopyridines of the formula I where $R^5$ is $C_1$–$C_8$-alkyl which may be interrupted by 1 or 2 oxygen atoms in ether function and is optionally hydroxyl- or phenyl-substituted, or allyl.

In the process of the invention, the first step (step 1) is carried out in the presence of an inert organic diluent and/or water. Suitable diluents are in particular those which are either completely immiscible with water or which are miscible with water only to a limited extent. Examples are isobutanol, toluene, o-, m- or p-xylene, ethylbenzene and mixtures thereof. The use of isobutanol, toluene or xylene is preferred.

Suitable bases for use in the first step are for example alkali metal carbonates or bicarbonates, such as sodium or potassium carbonate or bicarbonate. The use of sodium carbonate is preferred.

The second step (step 2) of the novel process is carried out at a pH from 3.5 to 6.5, preferably from 4 to 5.5. Since it is difficult to determine the pH in a melt, it is advisable, every time the pH of the melt is to be determined, to add a sample of the melt to water and to determine the pH of the aqueous system. The above-mentioned pH can be set not only with organic but also with inorganic acids. Suitable acids are for example sulfuric acid, hydrochloric acid and p-toluenesulfonic acid. The use of p-toluenesulfonic acid is preferred.

In the process of the invention the molar ratio of dichloropyridine II:amine III is from 1:1.03 to 1:1.5, preferably from 1:1.05 to 1:1.25, and the molar ratio of dichloropyridine II:aniline IV is from 1:1.3 to 1:3, preferably from 1:1.5 to 1:3.

Per mole of dichloropyridine II it is customary to use in the first step from 1 to 2 mole equivalents, preferably from 1 to 1.3 mole equivalents, of a base.

Based on the weight of dichloropyridine II the amount of inert organic diluent used in the first step is in general from 10 to 150% by weight, preferably from 30 to 100% by weight.

To initiate the second-stage reaction it is in general sufficient to employ catalytic amounts of an acid.

The process of the invention is conveniently carried out by starting in the first step with an initial charge of dichloropyridine II and inert organic diluent and raising the temperature with stirring initially to 10°–80° C., preferably 45°–70° C., in particular 45°–60° C. To this mixture is added at the stated temperature the amine III and then the base. Thereafter the reaction is carried out at the stated temperature. When the reaction has ended, which in general takes from 12 to 24 hours, the reaction mixture can be acidified, diluted with water and then freed of the diluent-water mixture. This can be done for example by distillation. The diluent thus recovered can be recycled into the process.

In the first step the diaminopyridines of the formula I are obtained as isomer mixtures consisting predominantly of a product of the formula I where $X^1$ is hydrogen and $X^2$ is cyano and to a minor proportion of a product of the formula I where $X^1$ is cyano and $X^2$ is hydrogen when the reaction is carried out at up to 55° C. for about 12 hours.

The predominant diaminopyridine I ($X^1$=H, $X^2$=CN) is preferably isolated in a practically isomer-free state before the diluent is separated off and the second step is started. This can be done for instance by filtering off since, for example if toluene is used as diluent, the product in question is in general in the form of a precipitate.

To prepare those diaminopyridines of the formula I where $R^5$ is an alkyl radical with a hydroxyl group, it is advisable in some cases to start not from the corresponding hydroxyalkylamines III but from their esterified compounds ($C_1$–$C_4$-alkanoyloxyalkyl compounds). Afterwards the alkanoyl group can be re-eliminated by hydrolysis.

By adding acid and aniline IV to the melt resulting from the removal of the diluent it is then possible to form the diaminopyridines I in the second step. The second reaction step is in general carried out at from 90° to 165° C., preferably at from 125° to 140° C. After the reaction has ended, which in general takes from 8 to 20 hours, the product is worked up.

This can be done in a conventional manner. For example, the reaction mixture can be diluted with water and isobutanol and be neutralized with a base, for example sodium hydroxide solution. Thereafter the water, the isobutanol and the excess aniline IV are distilled off under atmospheric pressure. The remaining aniline IV can be removed from the reaction mixture by distillation under reduced pressure. It is possible to recycle the aniline IV back into the reaction.

The resulting diaminopyridine of the formula I can either be further used in that form or be subjected to a reprecipitation. For this it is dissolved in concentrated hydrochloric acid and then reprecipitated with sodium hydroxide solution.

The process of the invention gives the diaminopyridines of the formula I in a simple manner and in high purity, in particular high isomer purity, and yield.

The diaminopyridines of the formula I are useful intermediates, in particular coupling components ($X^1$/$X^2$=H, CN), for the synthesis of dyes.

The Examples which follow illustrate the invention.

EXAMPLE 1

900 ml of isobutanol were mixed at room temperature with a mixture of 935 g of 2,6-diaminopyridine and 180 ml of water. Then the temperature is raised to 40° C. and a total of 479 g of 3-methoxypropylamine were added in the course of 1 hour with slight cooling. This was followed by stirring at from 40° to 45° C. for 2 hours, at which point 300 g of sodium carbonate were added. The mixture was stirred at from 40° to 45° C. for a further 2 hours and then the temperature was gradually raised to a maximum of 80° C. until the reaction has ended. The inorganic salts were then dissolved by adding 1000 ml of water, the mixture was acidified with sulfuric acid to pH 1, and the lower, aqueous layer, which contained the excess of amine, was separated off. The organic phase was then adjusted to pH 4–5 and then the isobutanol was removed by distillation. At 125° C. 1400 g of o-anisidine and 20 g of p-toluenesulfonic acid were added, and stirring was then continued at from 130° to 135° C. During the reaction the pH of a sample stirred into water/methanol was monitored. The pH of the reaction mixture was maintained within the range from 4.5 to 5.5 by the regular addition of anhydrous sodium carbonate to the reaction mixture. A total of 216 g of sodium carbonate were required. Then the reaction mixture was heated at 155° C. for 6 hours until the reaction has ended. The mixture was then cooled down to 110°–115° C., and 60 g of water were gradually added, as the result of which the reaction complex gave off carbon dioxide. After the evolution of carbon dioxide had ceased, the pH of the mixture was adjusted to 7–7.5 and the excess of o-anisidine was distilled off virtually quantitatively under reduced pressure. The residue was crystallized by adding a little ethylene diglycol monomethyl ether and, after precipitation with water, filtered off, washed and dried. Yield: 1460 g of product mixture of the formula

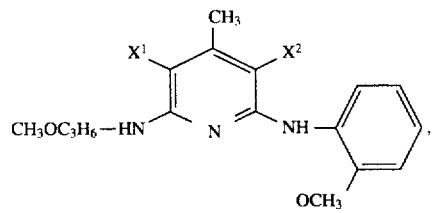

in which the isomer ratio of product 1 ($X^1$=H/$X^2$=CN):product 2 ($X^1$=CN/$X^2$=H) was 75:25.

EXAMPLE 2

Step 1

374 g of 2,6-dichloro-3-cyano-4-methylpyridine were added to 1000 ml of 70% by weight aqueous ethylamine solution at not more than 30° C. The mixture was stirred at from 15° to 30° C. for 3 hours, and then precipitated with ice, and the precipitate was filtered off, washed with water and dried. This gave a mixture of 2-chloro-3-cyano- 4-methyl-6-ethylaminopyridine (about 290 g) and 2-ethylamino-3-cyano-4-methyl-6-chloropyridine (about 96 g), which had a melting point of from 90° to 110° C. This mixture was dissolved in 600 ml of hot toluene. Cooling brought down a grayish white product of formula

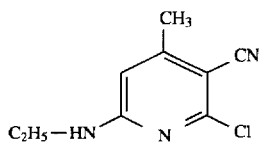

It was isolated by filtering with suction. Yield: 220 g, melting point: 128° C.

Step 2

Step 2 was carried out analogously to Example 1. The aniline derivative used was unsubstituted aniline.

This produced 270 g of a product of formula

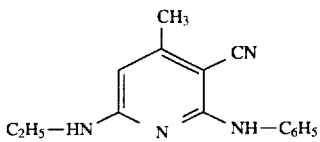

melting point: 96° C.

EXAMPLE 3

Step 1

440 g of 2,6-dichloro-3-cyano-4-methylpyridine were suspended in a mixture of 1000 ml of toluene and 300 ml of water. 230 g of 3-methoxypropylamine were then added at from 36° to 48° C. with cooling over 1 hour and the mixture was subsequently stirred at from 45° to 55° C. for 2 hours. The 141 g of sodium carbonate were added over 20 min and the mixture was subsequently stirred at from 45° to 55° C. for 10 hours and at 75° C. for a further 3 hours. It was then acidified with concentrated hydrochloric acid to about pH 1.5 and the bottom, aqueous layer was then separated off. This was followed by cooling to room temperature, followed by removal of the precipitated 2-chloro-3-cyano-4-methyl-6-(3-methoxypropylamino)-pyridine by filtration and isolation thereof as per Example 2.

This gave 370 g of a isomerically pure (3-cyano) product having a melting point of 106° C.

Step 2

Step 2 was carried out analogously to Example 1. The aniline derivative used was o-anisidine.

This gave 507 g of a product of the formula

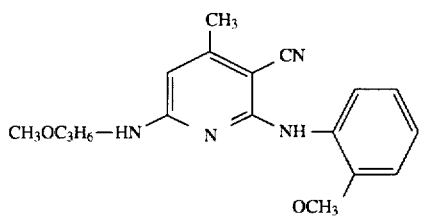

melting point: 120° C.

The same method gives the compounds of the formula

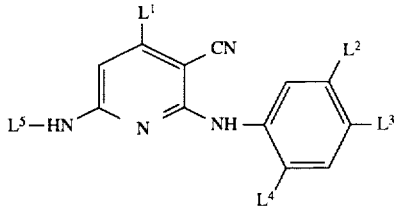

listed in the following table:

| Ex. No. | $L^1$ | $L^2$ | $L^3$ | $L^4$ | $L^5$ | mp. [°C.] |
|---|---|---|---|---|---|---|
| 4 | H | H | H | H | $C_3H_6OCH_3$ | 88 |
| 5 | $C_3H_7$ | H | H | H | $C_3H_6OCH_3$ | 75 |
| 6 | $CH_3$ | H | H | H | $C_2H_4OH$ | 140 |
| 7 | $CH_3$ | H | H | H | $C_4H_8OH$ | 68 |
| 8 | $CH_3$ | H | H | H | $CH(CH_3)CH_2OH$ | |
| 9 | $CH_3$ | H | H | H | $C_2H_5$ | |
| 10 | $CH_3$ | H | H | H | $C_2H_4OCH_3$ | 98 |
| 11 | $CH_3$ | H | H | H | $C_3H_6OC_2H_5$ | |
| 12 | $CH_3$ | H | H | H | $C_3H_6OCH(CH_3)_2$ | |
| 13 | $CH_3$ | H | H | H | $n-C_3H_7$ | 85 |
| 14 | $CH_3$ | H | H | H | $i-C_3H_7$ | 125 |
| 15 | $CH_3$ | H | H | H | $CH(CH_3)C_2H_5$ | |
| 16 | $CH_3$ | H | H | H | $n-C_4H_9$ | 45 |
| 17 | $CH_3$ | H | H | H | $CH_2CH=CH_2$ | |
| 18 | $CH_3$ | H | H | H | $C_2H_4OC_2H_5$ | |
| 19 | $CH_3$ | H | H | H | $C_2H_4OC_2H_4OH$ | |
| 20 | $CH_3$ | H | H | H | $n-C_5H_{11}$ | |
| 21 | $CH_3$ | H | H | H | ⟨N-H⟩ | |

-continued

| Ex. No. | L¹ | L² | L³ | L⁴ | L⁵ | mp. [°C.] |
|---|---|---|---|---|---|---|
| 22 | CH₃ | H | H | H | cyclohexyl (–C₆H₁₁) |  |
| 23 | CH₃ | H | H | H | C₃H₆OC₂H₄OCH₃ | Resin |
| 24 | CH₃ | H | H | H | CH₂C₆H₅ |  |
| 25 | CH₃ | H | H | H | C₂H₄C₆H₅ |  |
| 26 | CH₃ | H | H | H | CH(CH₃)CH₂C₆H₅ |  |
| 27 | CH₃ | H | H | H | C₂H₄–(tetrahydropyran-yl) | 120 |
| 28 | CH₃ | H | H | H | C₃H₆OC₄H₈OH | 40 |
| 29 | CH₃ | H | H | H | C₃H₆OC₂H₄OC₆H₅ |  |
| 30 | H | H | H | OCH₃ | C₃H₆OCH₃ | 76 |
| 31 | C₃H₇ | H | H | OCH₃ | C₃H₆OCH₃ | 55 |
| 32 | CH₃ | H | H | OCH₃ | C₂H₄OH |  |
| 33 | CH₃ | H | H | OCH₃ | C₃H₆OH |  |
| 34 | CH₃ | H | H | OCH₃ | CH(CH₃)CH₂OH |  |
| 35 | CH₃ | H | H | OCH₃ | C₂H₅ |  |
| 36 | CH₃ | H | H | OCH₃ | C₂H₄OCH₃ |  |
| 37 | CH₃ | H | H | OCH₃ | C₃H₆OC₂H₅ | 80 |
| 38 | CH₃ | H | H | OCH₃ | C₃H₆OCH(CH₃)₂ |  |
| 39 | CH₃ | H | H | OCH₃ | n-C₃H₇ | 80 |
| 40 | CH₃ | H | H | OCH₃ | i-C₃H₇ | 150 |
| 41 | CH₃ | H | H | OCH₃ | CH(CH₃)C₂H₅ |  |
| 42 | CH₃ | H | H | OCH₃ | n-C₄H₉ |  |
| 43 | CH₃ | H | H | OCH₃ | CH₂CH=CH₂ |  |
| 44 | CH₃ | H | H | OCH₃ | C₂H₄OC₂H₅ | 86 |
| 45 | CH₃ | H | H | OCH₃ | C₂H₄OC₂H₄OH |  |
| 46 | CH₃ | H | H | OCH₃ | n-C₅H₁₁ |  |
| 47 | CH₃ | H | H | OCH₃ | cyclopentyl |  |
| 48 | CH₃ | H | H | OCH₃ | cyclohexyl | 101 |
| 49 | CH₃ | H | H | OCH₃ | C₃H₆OC₂H₄OCH₃ | Resin |
| 50 | CH₃ | H | H | OCH₃ | CH₂C₆H₅ |  |
| 51 | CH₃ | H | H | OCH₃ | C₂H₄C₆H₅ |  |
| 52 | CH₃ | H | H | OCH₃ | CH(CH₃)CH₂C₆H₅ |  |
| 53 | CH₃ | H | H | OCH₃ | C₂H₄–(tetrahydropyran-yl) | 120 |
| 54 | CH₃ | H | H | OCH₃ | C₃H₆OC₂H₈OH |  |
| 55 | CH₃ | H | H | OCH₃ | C₃H₆OC₂H₄OC₆H₅ |  |
| 56 | H | H | OCH₃ | H | C₃H₆OCH₃ |  |
| 57 | C₃H₇ | H | OCH₃ | H | C₃H₆OCH₃ |  |
| 58 | CH₃ | H | OCH₃ | H | C₂H₄OH |  |
| 59 | CH₃ | H | OCH₃ | H | C₃H₆OH |  |
| 60 | CH₃ | H | OCH₃ | H | CH(CH₃)CH₂OH |  |
| 61 | CH₃ | H | OCH₃ | H | C₂H₅ |  |
| 62 | CH₃ | H | OCH₃ | H | C₂H₄OCH₃ |  |
| 63 | CH₃ | H | OCH₃ | H | C₃H₆OC₂H₅ |  |
| 64 | CH₃ | H | OCH₃ | H | C₃H₆OCH(CH₃)₂ |  |
| 65 | CH₃ | H | OCH₃ | H | n-C₃H₇ |  |
| 66 | CH₃ | H | OCH₃ | H | i-C₃H₇ | 135 |
| 67 | CH₃ | H | OCH₃ | H | CH(CH₃)C₂H₅ |  |
| 68 | CH₃ | H | OCH₃ | H | n-C₄H₉ |  |
| 69 | CH₃ | H | OCH₃ | H | CH₂CH=CH₂ |  |
| 70 | CH₃ | H | OCH₃ | H | C₂H₄OC₂H₅ |  |
| 71 | CH₃ | H | OCH₃ | H | C₂H₄OC₂H₄OH |  |
| 72 | CH₃ | H | OCH₃ | H | n-C₅H₁₁ |  |

-continued

| Ex. No. | L¹ | L² | L³ | L⁴ | L⁵ | mp. [°C.] |
|---|---|---|---|---|---|---|
| 73 | $CH_3$ | H | $OCH_3$ | H | cyclopentyl-H | |
| 74 | $CH_3$ | H | $OCH_3$ | H | cyclohexyl-H | |
| 75 | $CH_3$ | H | $OCH_3$ | H | $C_3H_6OC_2H_4OCH_3$ | Resin |
| 76 | $CH_3$ | H | $OCH_3$ | H | $CH_2C_6H_5$ | |
| 77 | $CH_3$ | H | $OCH_3$ | H | $C_2H_4C_6H_5$ | |
| 78 | $CH_3$ | H | $OCH_3$ | H | $CH(CH_3)CH_2C_6H_5$ | |
| 79 | $CH_3$ | H | $OCH_3$ | H | $C_2H_4$-tetrahydropyranyl-O | |
| 80 | $CH_3$ | H | $OCH_3$ | H | $C_3H_6OC_4H_8OH$ | |
| 81 | $CH_3$ | H | $OCH_3$ | H | $C_3H_6OC_2H_4OC_6H_5$ | |
| 82 | H | $OCH_3$ | H | H | $C_3H_6OCH_3$ | |
| 83 | $C_3H_7$ | $OCH_3$ | H | H | $C_3H_6OCH_3$ | |
| 84 | $CH_3$ | $OCH_3$ | H | H | $C_2H_4OH$ | |
| 85 | $CH_3$ | $OCH_3$ | H | H | $C_3H_6OH$ | |
| 86 | $CH_3$ | $OCH_3$ | H | H | $CH(CH_3)CH_2OH$ | |
| 87 | $CH_3$ | $OCH_3$ | H | H | $C_2H_5$ | |
| 88 | $CH_3$ | $OCH_3$ | H | H | $C_2H_4OCH_3$ | |
| 89 | $CH_3$ | $OCH_3$ | H | H | $C_3H_6OC_2H_5$ | |
| 90 | $CH_3$ | $OCH_3$ | H | H | $C_3H_6OCH(CH_3)_2$ | Resin |
| 91 | $CH_3$ | $OCH_3$ | H | H | $n\text{-}C_3H_7$ | |
| 92 | $CH_3$ | $OCH_3$ | H | H | $i\text{-}C_3H_7$ | |
| 93 | $CH_3$ | $OCH_3$ | H | H | $CH(CH_3)C_2H_5$ | |
| 94 | $CH_3$ | $OCH_3$ | H | H | $n\text{-}C_4H_9$ | |
| 95 | $CH_3$ | $OCH_3$ | H | H | $CH_2CH=CH_2$ | |
| 96 | $CH_3$ | $OCH_3$ | H | H | $C_2H_4OC_2H_5$ | |
| 97 | $CH_3$ | $OCH_3$ | H | H | $C_2H_{4L\ OC2H4}OH$ | |
| 98 | $CH_3$ | $OCH_3$ | H | H | $n\text{-}C_5H_{11}$ | |
| 99 | $CH_3$ | $OCH_3$ | H | H | cyclopentyl-H | |
| 100 | $CH_3$ | $OCH_3$ | H | H | cyclohexyl-H | |
| 101 | $CH_3$ | $OCH_3$ | H | H | $C_3H_6OC_2H_4OCH_3$ | |
| 102 | $CH_3$ | $OCH_3$ | H | H | $CH_2C_6H_5$ | |
| 103 | $CH_3$ | $OCH_3$ | H | H | $C_2H_{4L\ C6}H_5$ | |
| 104 | $CH_3$ | $OCH_3$ | H | H | $CH(CH_3)CH_2C_6H_5$ | |
| 105 | $CH_3$ | O | H | $CH_3$ | $C_2H_4$-tetrahydropyranyl-O | |
| 106 | $CH_3$ | $OCH_3$ | H | H | $C_3H_6OC_4H_8OH$ | |
| 107 | $CH_3$ | $OCH_3$ | H | H | $C_3H_6OC_2H_4OC_6H_5$ | |
| 108 | $CH_3$ | $CH_3$ | H | $OCH_3$ | $C_3H_6OCH_3$ | 86 |
| 109 | $C_3H_7$ | $CH_3$ | H | $OCH_3$ | $C_3H_6OCH_3$ | |
| 110 | $CH_3$ | $CH_3$ | H | $OCH_3$ | $C_2H_4OH$ | |
| 111 | $CH_3$ | $CH_3$ | H | $OCH_3$ | $C_3H_6OH$ | |
| 112 | $CH_3$ | $CH_3$ | H | $OCH_3$ | $CH(CH_3)CH_2OH$ | |
| 113 | $CH_3$ | $CH_3$ | H | $OCH_3$ | $C_2H_5$ | |
| 114 | $CH_3$ | $CH_3$ | H | $OCH_3$ | $C_2H_4OCH_3$ | |
| 115 | $CH_3$ | $CH_3$ | H | $OCH_3$ | $C_3H_6OC_2H_5$ | 75 |
| 116 | $CH_3$ | $CH_3$ | H | $OCH_3$ | $C_3H_6OCH(CH_3)_2$ | Resin |
| 117 | $CH_3$ | $CH_3$ | H | $OCH_3$ | $n\text{-}C_3H_7$ | 147 |
| 118 | $CH_3$ | $CH_3$ | H | $OCH_3$ | $i\text{-}C_3H_7$ | 150 |
| 119 | $CH_3$ | $CH_3$ | H | $OCH_3$ | $CH(CH_3)C_2H_5$ | |
| 120 | $CH_3$ | $CH_3$ | H | $OCH_3$ | $n\text{-}C_4H_9$ | |
| 121 | $CH_3$ | $CH_3$ | H | $OCH_3$ | $CH_2CH=CH_2$ | |
| 122 | $CH_3$ | $CH_3$ | H | $OCH_3$ | $C_2H_4OC_2H_5$ | 95 |

-continued

| Ex. No. | L¹ | L² | L³ | L⁴ | L⁵ | mp. [°C.] |
|---|---|---|---|---|---|---|
| 123 | CH₃ | CH₃ | H | OCH₃ | C₂H₄OC₂H₄OH | |
| 124 | CH₃ | CH₃ | H | OCH₃ | n-C₅H₁₁ | |
| 125 | CH₃ | CH₃ | H | OCH₃ | cyclopentyl-H | |
| 126 | CH₃ | CH₃ | H | OCH₃ | cyclohexyl-H | |
| 127 | CH₃ | CH₃ | H | OCH₃ | C₃H₆OC₂H₄OCH₃ | |
| 128 | CH₃ | CH₃ | H | OCH₃ | CH₂C₆H₅ | |
| 129 | CH₃ | CH₃ | H | OCH₃ | C₂H₄C₆H₅ | |
| 130 | CH₃ | CH₃ | H | OCH₃ | CH(CH₃)CH₂C₆H₅ | |
| 131 | CH₃ | CH₃ | H | OCH₃ | C₂H₄-(tetrahydropyran-yl) | 116 |
| 132 | CH₃ | CH₃ | H | OCH₃ | C₃H₆OC₄H₈OH | |
| 133 | CH₃ | CH₃ | H | OCH₃ | C₃H₆OC₂H₄OC₆H₅ | |
| 134 | H | H | H | CH₃ | C₃H₆OCH₃ | |
| 135 | C₃H₇ | H | H | CH₃ | C₃H₆OCH₃ | |
| 136 | CH₃ | H | H | CH₃ | C₂H₄OH | |
| 137 | CH₃ | H | H | CH₃ | C₃H₆OH | |
| 138 | CH₃ | H | H | CH₃ | CH(CH₃)CH₂OH | |
| 139 | CH₃ | H | H | CH₃ | C₂H₅ | |
| 140 | CH₃ | H | H | CH₃ | C₂H₄OCH₃ | |
| 141 | CH₃ | H | H | CH₃ | C₃H₆OC₂H₅ | |
| 142 | CH₃ | H | H | CH₃ | C₃H₆OCH(CH₃)₂ | Resin |
| 143 | CH₃ | H | H | CH₃ | n-C₃H₇ | 92 |
| 144 | CH₃ | H | H | CH₃ | i-C₃H₇ | |
| 145 | CH₃ | H | H | CH₃ | CH(CH₃)C₂H₅ | |
| 146 | CH₃ | H | H | CH₃ | n-C₄H₉ | |
| 147 | CH₃ | H | H | CH₃ | CH₂CH=CH₂ | |
| 148 | CH₃ | H | H | CH₃ | C₂H₄OC₂H₅ | |
| 149 | CH₃ | H | H | CH₃ | C₂H₄OC₂H₄OH | |
| 150 | CH₃ | H | H | CH₃ | n-C₅H₁₁ | |
| 151 | CH₃ | H | H | CH₃ | cyclopentyl-H | |
| 152 | CH₃ | H | H | CH₃ | cyclohexyl-H | |
| 153 | CH₃ | H | H | CH₃ | C₃H₆OC₂H₄OCH₃ | Resin |
| 154 | CH₃ | H | H | CH₃ | CH₂C₆H₅ | |
| 155 | CH₃ | H | H | CH₃ | C₂H₄C₆H₅ | |
| 156 | CH₃ | H | H | CH₃ | CH(CH₃)CH₂C₆H₅ | |
| 157 | CH₃ | H | H | CH₃ | C₂H₄-(tetrahydropyran-yl) | 112 |
| 158 | CH₃ | H | H | CH₃ | C₃H₆OC₄H₈OH | |
| 159 | CH₃ | H | H | CH₃ | C₃H₆OC₂H₄OC₆H₅ | |
| 160 | H | H | CH₃ | CH₃ | C₃H₆OCH₃ | |
| 161 | C₃H₇ | H | CH₃ | CH₃ | C₃H₆OCH₃ | |
| 162 | CH₃ | H | CH₃ | CH₃ | C₂H₄OH | |
| 163 | CH₃ | H | CH₃ | CH₃ | C₃H₆OH | |
| 164 | CH₃ | H | CH₃ | CH₃ | CH(CH₃)CH₂OH | |
| 165 | CH₃ | H | CH₃ | CH₃ | C₂H₅ | |
| 166 | CH₃ | H | CH₃ | CH₃ | C₂H₄OCH₃ | |
| 167 | CH₃ | H | CH₃ | CH₃ | C₃H₆OC₂H₅ | |
| 168 | CH₃ | H | CH₃ | CH₃ | C₃H₆OCH(CH₃)₂ | Resin |
| 169 | CH₃ | H | CH₃ | CH₃ | n-C₃H₇ | |
| 170 | CH₃ | H | CH₃ | CH₃ | i-C₃H₇ | |
| 171 | CH₃ | H | CH₃ | CH₃ | CH(CH₃)C₂H₅ | |

-continued

| Ex. No. | L¹ | L² | L³ | L⁴ | L⁵ | mp. [°C.] |
|---|---|---|---|---|---|---|
| 172 | $CH_3$ | H | $CH_3$ | $CH_3$ | $n-C_4H_9$ | |
| 173 | $CH_3$ | H | $CH_3$ | $CH_3$ | $CH_2CH=CH_2$ | |
| 174 | $CH_3$ | H | $CH_3$ | $CH_3$ | $C_2H_4OC_2H_5$ | |
| 175 | $CH_3$ | H | $CH_3$ | $CH_3$ | $C_2H_4OC_2H_4OH$ | |
| 176 | $CH_3$ | H | $CH_3$ | $CH_3$ | $n-C_5H_{11}$ | |
| 177 | $CH_3$ | H | $CH_3$ | $CH_3$ | cyclopentyl | |
| 178 | $CH_3$ | H | $CH_3$ | $CH_3$ | cyclohexyl | |
| 179 | $CH_3$ | H | $CH_3$ | $CH_3$ | $C_3H_6OC_2H_4OCH_3$ | Resin |
| 180 | $CH_3$ | H | $CH_3$ | $CH_3$ | $CH_2C_6H_5$ | |
| 181 | $CH_3$ | H | $CH_3$ | $CH_3$ | $C_2H_4C_6H_5$ | |
| 182 | $CH_3$ | H | $CH_3$ | $CH_3$ | $CH(CH_3)CH_2C_6H_5$ | |
| 183 | $CH_3$ | H | $CH_3$ | $CH_3$ | $C_2H_4$-(tetrahydropyranyl) | 110 |
| 184 | $CH_3$ | H | $CH_3$ | $CH_3$ | $C_3H_6OC_4H_8OH$ | |
| 185 | $CH_3$ | H | $CH_3$ | $CH_3$ | $C_3H_6OC_2H_4OC_6H_5$ | |
| 186 | H | $CH_3$ | H | $CH_3$ | $C_3H_6OCH_3$ | |
| 187 | $C_3H_7$ | $CH_3$ | H | $CH_3$ | $C_3H_6OCH_3$ | |
| 188 | $CH_3$ | $CH_3$ | H | $CH_3$ | $C_2H_4OH$ | |
| 189 | $CH_3$ | $CH_3$ | H | $CH_3$ | $C_3H_6OH$ | |
| 190 | $CH_3$ | $CH_3$ | H | $CH_3$ | $CH(CH_3)CH_2OH$ | |
| 191 | $CH_3$ | $CH_3$ | H | $CH_3$ | $C_2H_5$ | |
| 192 | $CH_3$ | $CH_3$ | H | $CH_3$ | $C_2H_4OCH_3$ | |
| 193 | $CH_3$ | $CH_3$ | H | $CH_3$ | $C_3H_6OC_2H_5$ | |
| 194 | $CH_3$ | $CH_3$ | H | $CH_3$ | $C_3H_6OCH(CH_3)_2$ | |
| 195 | $CH_3$ | $CH_3$ | H | $CH_3$ | $n-C_3H_7$ | |
| 196 | $CH_3$ | $CH_3$ | H | $CH_3$ | $i-C_3H_7$ | |
| 197 | $CH_3$ | $CH_3$ | H | $CH_3$ | $CH(CH_3)C_2H_5$ | |
| 198 | $CH_3$ | $CH_3$ | H | $CH_3$ | $n-C_4H_9$ | |
| 199 | $CH_3$ | $CH_3$ | H | $CH_3$ | $CH_2CH=CH_2$ | |
| 200 | $CH_3$ | $CH_3$ | H | $CH_3$ | $C_2H_4OC_2H_5$ | |
| 201 | $CH_3$ | $CH_3$ | H | $CH_3$ | $C_2H_4OC_2H_4OH$ | |
| 202 | $CH_3$ | $CH_3$ | H | $CH_3$ | $n-C_5H_{11}$ | |
| 203 | $CH_3$ | $CH_3$ | H | $CH_3$ | cyclopentyl | |
| 204 | $CH_3$ | $CH_3$ | H | $CH_3$ | cyclohexyl | |
| 205 | $CH_3$ | $CH_3$ | H | $CH_3$ | $C_3H_6OC_2H_4OCH_3$ | Resin |
| 206 | $CH_3$ | $CH_3$ | H | $CH_3$ | $CH_2C_6H_5$ | |
| 207 | $CH_3$ | $CH_3$ | H | $CH_3$ | $C_2H_4C_6H_5$ | |
| 208 | $CH_3$ | $CH_3$ | H | $CH_3$ | $CH(CH_3)CH_2C_6H_5$ | |
| 209 | $CH_3$ | $CH_3$ | H | $CH_3$ | $C_2H_4$-(tetrahydropyranyl) | |
| 210 | $CH_3$ | $CH_3$ | H | $CH_3$ | $C_3H_6OC_4H_8OH$ | 35 |
| 211 | $CH_3$ | $CH_3$ | H | $CH_3$ | $C_3H_6OC_2H_4OC_6H_5$ | |
| 212 | H | H | $C_2H_5$ | H | $C_3H_6OCH_3$ | |
| 213 | $C_3H_7$ | H | $C_2H_5$ | H | $C_3H_6OCH_3$ | |
| 214 | $CH_3$ | H | $C_2H_5$ | H | $C_2H_4OH$ | |
| 215 | $CH_3$ | H | $C_2H_5$ | H | $C_3H_6OH$ | |
| 216 | $CH_3$ | H | $C_2H_5$ | H | $CH(CH_3)CH_2OH$ | |
| 217 | $CH_3$ | H | $C_2H_5$ | H | $C_2H_5$ | |
| 218 | $CH_3$ | H | $C_2H_5$ | H | $C_2H_4OCH_3$ | |
| 219 | $CH_3$ | H | $C_2H_5$ | H | $C_3H_6OC_2H_5$ | |
| 220 | $CH_3$ | H | $C_2H_5$ | H | $C_3H_6OCH(CH_3)_2$ | Resin |

-continued

| Ex. No. | L¹ | L² | L³ | L⁴ | L⁵ | mp. [°C.] |
|---|---|---|---|---|---|---|
| 221 | $CH_3$ | H | $C_2H_5$ | H | $n$-$C_3H_7$ | |
| 222 | $CH_3$ | H | $C_2H_5$ | H | $i$-$C_3H_7$ | |
| 223 | $CH_3$ | H | $C_2H_5$ | H | $CH(CH_3)C_2H_5$ | |
| 224 | $CH_3$ | H | $C_2H_5$ | H | $n$-$C_4H_9$ | |
| 225 | $CH_3$ | H | $C_2H_5$ | H | $CH_2CH=CH_2$ | |
| 226 | $CH_3$ | H | $C_2H_5$ | H | $C_2H_4OC_2H_5$ | |
| 227 | $CH_3$ | H | $C_2H_5$ | H | $C_2H_4OC_2H_4OH$ | |
| 228 | $CH_3$ | H | $C_2H_5$ | H | $n$-$C_5H_{11}$ | |
| 229 | $CH_3$ | H | $C_2H_5$ | H |  | |
| 230 | $CH_3$ | H | $CH_3$ | H | 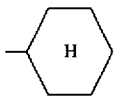 | 130 |
| 231 | $CH_3$ | H | $C_2H_5$ | H | $C_3H_6OC_2H_{4L\ OCH3}$ | |
| 232 | $CH_3$ | H | $C_2H_5$ | H | $CH_2C_6H_5$ | |
| 233 | $CH_3$ | H | $C_2H_5$ | H | $C_2H_4C_6H_5$ | |
| 234 | $CH_3$ | H | $C_2H_5$ | H | $CH(CH_3)CH_2C_6H_5$ | |
| 235 | $CH_3$ | H | $C_2H_5$ | H | 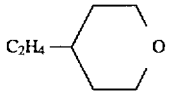 | 108 |
| 236 | $CH_3$ | H | $C_2H_5$ | H | $C_3H_6OC_4H_8OH$ | 36 |
| 237 | $CH_3$ | H | $C_2H_5$ | H | $C_3H_6OC_2H_4OC_6H_5$ | |
| 238 | H | $CH_3$ | H | H | $C_3H_6OCH_3$ | |
| 239 | $C_3H_7$ | $CH_3$ | H | H | $C_3H_6OCH_3$ | |
| 240 | $CH_3$ | $CH_3$ | H | H | $C_2H_4OH$ | |
| 241 | $CH_3$ | $CH_3$ | H | H | $C_3H_6OH$ | |
| 242 | $CH_3$ | $CH_3$ | H | H | $CH(CH_3)CH_2OH$ | |
| 243 | $CH_3$ | $CH_3$ | H | H | $C_2H_5$ | |
| 244 | $CH_3$ | $CH_3$ | H | H | $C_2H_4OCH_3$ | |
| 245 | $CH_3$ | $CH_3$ | H | H | $C_3H_6OC_2H_5$ | |
| 246 | $CH_3$ | $CH_3$ | H | H | $C_3H_6OCH(CH_3)_2$ | Resin |
| 247 | $CH_3$ | $CH_3$ | H | H | $n$-$C_3H_7$ | |
| 248 | $CH_3$ | $CH_3$ | H | H | $i$-$C_3H_7$ | 105 |
| 249 | $CH_3$ | $CH_3$ | H | H | $CH(CH_3)C_2H_5$ | |
| 250 | $CH_3$ | $CH_3$ | H | H | $n$-$C_4H_9$ | |
| 251 | $CH_3$ | $CH_3$ | H | H | $CH_2CH=CH_2$ | |
| 252 | $CH_3$ | $CH_3$ | H | H | $C_2H_4OC_2H_5$ | |
| 253 | $CH_3$ | $CH_3$ | H | H | $C_2H_4OC_2H_4OH$ | |
| 254 | $CH_3$ | $CH_3$ | H | H | $n$-$C_5H_{11}$ | |
| 255 | $CH_3$ | $CH_3$ | H | H |  | |
| 256 | $CH_3$ | $CH_3$ | H | H | 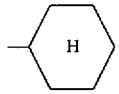 | 110 |
| 257 | $CH_3$ | $CH_3$ | H | H | $C_3H_6OC_2H_4OCH_3$ | |
| 258 | $CH_3$ | $CH_3$ | H | H | $CH_2C_6H_5$ | |
| 259 | $CH_3$ | $CH_3$ | H | H | $C_2H_4C_6H_5$ | |
| 260 | $CH_3$ | $CH_3$ | H | H | $CH(CH_3)CH_2C_6H_5$ | |
| 261 | $CH_3$ | $CH_3$ | H | H |  | 127 |
| 262 | $CH_3$ | $CH_3$ | H | H | $C_3H_6OC_4H_8OH$ | |
| 263 | $CH_3$ | $CH_3$ | H | H | $C_3H_6OC_2H_4OC_6H_5$ | |
| 264 | $CH_3$ | H | H | H | $C_3H_6OC_4H_8OH$ | |
| 265 | $CH_3$ | H | $n$-$C_4H_9$ | H | $i$-$C_3H_7$ | 92 (hydrochloride) |
| 266 | $CH_3$ | H | H | $OCH_3$ | $CH(C_2H_5)CH_2OCH_3$ | 46 |

-continued

| Ex. No. | $L^1$ | $L^2$ | $L^3$ | $L^4$ | $L^5$ | mp. [°C.] |
|---|---|---|---|---|---|---|
| 267 | $CH_3$ | H | H | $OCH_3$ | 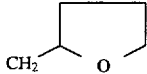 | 105 |
| 268 | $CH_3$ | H | H | h | $CH(CH_3)CH_2OCH_3$ | 120 (pure isomer) |
| 269 | $CH_3$ | H | H | H | $CH(CH_3)CH_2OCH_3$ | 114 (mixed isomers) |
| 270 | $CH_3$ | H | $OCH_3$ | H | $CH(CH_3)CH_2OCH_3$ | 90 |
| 271 | $CH_3$ | H | $CH_3$ | H | $CH(CH_3)CH_2OCH_3$ | 110 |
| 272 | $CH_3$ | H | H | H | $CH(CH_3)CH_2OCH_3$ | 114 |
| 273 | $CH_3$ | H | H | H | $CH(CH_3)CH_2OCH_3$ | 80 |

We claim:

1. A process for preparing diaminopyridines of the formula I

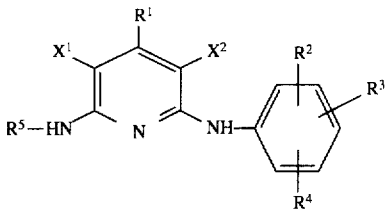

where
one of the two radicals $X^1$ and $X^2$ is hydrogen, $C_1$–$C_4$-alkyl, halogen or nitro and the other is cyano,
$R^1$ is hydrogen, $C_1$–$C_4$-alkyl or phenyl,
$R^2$ and $R^3$ are each independently of one another hydrogen, $C_1$–$C_4$-alkyl or $C_1$–$C_4$-alkoxy,
$R^4$ is hydrogen or $C_1$–$C_4$-alkyl, and
$R^5$ is $C_1$–$C_{10}$-alkyl which may be interrupted by from 1 to 3 oxygen atoms in ether function and is optionally hydroxyl-, $C_1$–$C_4$-alkanoyloxy-, phenoxy-, phenyl-, tetrahydrofuranyl- or tetrahydropyranyl-substituted, $C_3$–$C_4$-alkenyl or $C_5$–$C_7$-cycloalkyl,
by reacting dichloropyridines of the formula II

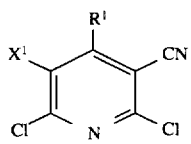

where $R^1$ and $X^1$ are each as defined above, with amines by reacting in a first step a dichloropyridine of the formula II with an amine of the formula III $$R^5-NH_2 \quad \text{(III)}$$

where $R^5$ is as defined above, at from 10° to 80° C. in the presence of a base and of an inert organic diluent and/or water, then removing the diluent and thereafter, with or without prior intermediate isolation of the reaction product, reacting it in a second step with an aniline of the formula IV

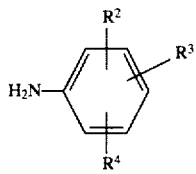

where $R^2$, $R^3$ and $R^4$ are each as defined above, which comprises carrying out the second step in a melt at from 90° to 165° C. and at a pH from 3.5 to 6.5 using from 1.3 to 3 mol of aniline IV are used per mole of dichloropyridine II.

2. A process as claimed in claim 1, wherein in the formula I, $X^1$ is hydrogen and $X^2$ is cyano.

3. A process as claimed in claim 1, wherein in the formula I, $R^1$ is methyl.

4. A process as claimed in claim 1, wherein the diluent used in the first step is isobutanol, toluene, o-, m- or p-xylene, ethylbenzene or a mixture thereof.

* * * * *